(12) United States Patent
Johnson et al.

(10) Patent No.: US 11,518,971 B2
(45) Date of Patent: Dec. 6, 2022

(54) METHOD AND APPARATUS FOR SPATIAL CONTROL OF CELLULAR GROWTH

(71) Applicant: RESEARCH TRIANGLE INSTITUTE, Research Triangle Park, NC (US)

(72) Inventors: Leah Marie Johnson, Durham, NC (US); Ninell Pollas Mortensen, Holly Springs, NC (US); Ginger Denison Rothrock, Cary, NC (US); Nicolas D. Huffman, Raleigh, NC (US)

(73) Assignee: RESEARCH TRIANGLE INSTITUTE, Research Triangle Park, NC (US)

( * ) Notice: Subject to any disclaimer, the term of this patent is extended or adjusted under 35 U.S.C. 154(b) by 338 days.

(21) Appl. No.: 16/695,550

(22) Filed: Nov. 26, 2019

(65) Prior Publication Data

US 2020/0165555 A1    May 28, 2020

Related U.S. Application Data

(60) Provisional application No. 62/771,958, filed on Nov. 27, 2018.

(51) Int. Cl.
*C12M 1/00* (2006.01)
*B29C 64/40* (2017.01)
(Continued)

(52) U.S. Cl.
CPC ............. *C12M 23/02* (2013.01); *B29C 64/40* (2017.08); *C12N 5/0068* (2013.01);
(Continued)

(58) Field of Classification Search
CPC ... B29C 33/52; B29C 33/033; B29C 45/4457; B29C 2043/3668; B29C 39/10;
(Continued)

(56) References Cited

U.S. PATENT DOCUMENTS

| 8,129,188 B2 | 3/2012 | Shih et al. |
| 8,463,418 B2 | 6/2013 | Liu et al. |

(Continued)

FOREIGN PATENT DOCUMENTS

| CN | 101007999 A | 8/2007 |
| CN | 101199436 A | 6/2008 |

(Continued)

*Primary Examiner* — Jeffrey M Wollschlager
(74) *Attorney, Agent, or Firm* — Hultquist, PLLC; Steven J. Hultquist

(57) ABSTRACT

A three-dimensional cell growth containment article is described, which includes a molded body channelized by removal of sacrificial channelizing element(s) therefrom, so that the molded body contains one or more channel(s) therein, with a matrix material in at least one of such channel(s) that is supportive of three-dimensional cell growth in the matrix material. A method for making such articles is also described, in which a molded body is formed with one or more sacrificial channelizing element(s) therein, following which the sacrificial channelizing element(s) are removed. The three-dimensional cell growth containment articles of the present disclosure may be utilized in any applications in which there exists a need to reproducibly generate three-dimensional cellular structures, e.g., islet transplantation for diabetes treatment, transplantation of hormone secreting cells, cellular scaffolds for wound healing, and generation of tissue engineering structures to regain structural usefulness for orthopedic applications.

12 Claims, 7 Drawing Sheets
(6 of 7 Drawing Sheet(s) Filed in Color)

(51) Int. Cl.
*C12N 5/00* (2006.01)
*B29K 23/00* (2006.01)
*B29K 71/00* (2006.01)
*B29K 67/00* (2006.01)

(52) U.S. Cl.
CPC .. *B29K 2023/083* (2013.01); *B29K 2067/046* (2013.01); *B29K 2071/00* (2013.01); *C12N 2500/33* (2013.01); *C12N 2500/50* (2013.01)

(58) Field of Classification Search
CPC .. B29C 39/26–38; B29C 64/40; C12M 23/02; C12M 23/20; C12M 23/14; B01J 19/0093; C12N 5/0068; C12N 2500/33; C12N 2500/50; C12N 2533/74; C12N 5/0062; B29K 2023/083; B29K 2067/046; B29K 2071/00
See application file for complete search history.

(56) References Cited

U.S. PATENT DOCUMENTS

| | | | |
|---|---|---|---|
| 2003/0015816 A1* | 1/2003 | Rapacki | A61F 2/2493 264/102 |
| 2003/0214057 A1* | 11/2003 | Huang | B01L 3/502707 425/808 |
| 2006/0173394 A1* | 8/2006 | Stroock | A61L 27/20 602/41 |
| 2006/0270783 A1* | 11/2006 | Beck | F16L 11/06 524/564 |
| 2007/0048737 A1 | 3/2007 | Rouquet et al. | |
| 2010/0129912 A1 | 5/2010 | Su et al. | |
| 2011/0049754 A1* | 3/2011 | Mahaffy | B29C 33/3857 700/98 |
| 2011/0196660 A1 | 8/2011 | Liu et al. | |
| 2013/0029422 A1 | 1/2013 | Goral et al. | |
| 2014/0106454 A1* | 4/2014 | Lenardi | B81C 1/00523 435/396 |
| 2014/0155552 A1* | 6/2014 | Oriani | C08L 23/0853 525/178 |
| 2015/0087004 A1 | 3/2015 | Chen et al. | |
| 2016/0263781 A1* | 9/2016 | Gerardi | A61F 2/16 |
| 2017/0166862 A1 | 6/2017 | Shen et al. | |
| 2017/0204136 A1 | 7/2017 | Dhara et al. | |
| 2017/0282464 A1* | 10/2017 | Stadler | B29C 48/303 |
| 2018/0024120 A1* | 1/2018 | Levner | C12N 5/0658 514/1.1 |
| 2018/0092388 A1* | 4/2018 | Hukelmann | A22C 13/00 |
| 2021/0170667 A1* | 6/2021 | Lee | B29C 59/021 |

FOREIGN PATENT DOCUMENTS

| | | |
|---|---|---|
| CN | 101245313 A | 8/2008 |
| CN | 102292384 A | 12/2011 |
| CN | 102517247 A | 6/2012 |
| CN | 102847197 A | 1/2013 |
| CN | 203802865 U | 9/2014 |
| CN | 107304409 A | 10/2017 |
| CN | 107904172 A | 4/2018 |
| EP | 1326968 B1 | 4/2007 |
| IN | 201631001353 | 1/2016 |
| JP | 2004216119 A | 8/2004 |
| JP | 3599341 B2 | 12/2004 |
| JP | 2007518710 A | 7/2007 |
| JP | 2007518710 A | 8/2007 |
| JP | 4238972 B2 | 3/2009 |
| JP | 2010517590 A | 5/2010 |
| JP | 2010148496 A | 7/2010 |
| JP | 2011239756 A | 12/2011 |
| JP | 5283606 B2 | 9/2013 |
| JP | 5691240 B2 | 4/2015 |
| KR | 20060124654 A | 12/2006 |
| KR | 101131303 B1 | 3/2012 |
| KR | 20120094488 A | 8/2012 |
| KR | 20140125662 A | 10/2014 |
| KR | 20160021352 A | 2/2016 |
| KR | 20160034540 A | 3/2016 |
| KR | 101839909 B1 | 3/2018 |
| TW | 200720433 A | 6/2007 |
| TW | 201335368 A | 9/2013 |
| WO | WO9948541 A | 9/1999 |
| WO | WO2008101001 A2 | 8/2008 |
| WO | WO2009026200 A1 | 2/2009 |
| WO | WO2010059902 A2 | 5/2010 |
| WO | WO2013015939 A1 | 1/2013 |
| WO | WO2013050921 A1 | 4/2013 |
| WO | WO2013116729 A1 | 8/2013 |
| WO | WO2013156941 A1 | 10/2013 |
| WO | WO2014105581 A1 | 7/2014 |
| WO | WO2014171782 A1 | 10/2014 |
| WO | WO2015080670 A1 | 6/2015 |
| WO | WO2015137595 A1 | 9/2015 |
| WO | WO2015152612 A1 | 10/2015 |
| WO | WO2016043489 A1 | 3/2016 |
| WO | WO2017107837 A1 | 6/2017 |
| WO | WO2017122216 A1 | 7/2017 |

\* cited by examiner

METHOD AND APPARATUS FOR SPATIAL CONTROL OF CELLULAR GROWTH

CROSS-REFERENCE TO RELATED APPLICATION

The benefit under 35 USC § 119 of U.S. Provisional Patent Application 62/771,958 filed Nov. 27, 2018 in the names of Leah Marie Johnson, Ninell Pollas Mortensen, Ginger Denison Rothrock, and Nicolas D. Huffman for METHOD AND APPARATUS FOR SPATIAL CONTROL OF CELLULAR GROWTH is hereby claimed. The disclosure of U.S. Provisional Patent Application 62/771,958 is hereby incorporated herein by reference, in its entirety, for all purposes.

FIELD

The present disclosure relates to three-dimensional cell growth containment articles useful in retentive deployment of cells, e.g., for culturing of cell populations to produce secreted therapeutic agents, and to methods of making and using such articles.

DESCRIPTION OF THE RELATED ART

In many biological fields of endeavor, there exists a need to provide a cellular population whose growth is controllably managed and maintained. In specific, there is a need for temporally and spatially controlling cell growth in a wide variety of applications.

An ability to spatially and temporally guide cellular growth affords vast possibilities in research as well as clinical applications, in fields as diverse as tissue engineering, therapeutic treatment and prevention, biomechanics, cellular biology, and cell signaling. Cellular viability and proliferation depends on a multitude of conditions, including for example oxygenation, nutrient accessibility, cellular cues, and biocompatible environments.

Typically, three-dimensional growth of cellular cultures can be carried out using a polymeric matrix, in which the cells are seated onto the matrix and provide cues to guide cellular proliferation. Cells can be seated directly onto pre-form polymers, or alternatively incorporated into a monomer mixture prior to polymerization using in-situ cell culture methods. Polymer matrices may for example be constituted by hydrogels that can be fabricated using light-initiated free radical cross-linking, Michaels-type addition cross-linking, or redox-initiated cross-linking techniques, or ionic cross-linking methods such as the use of alginate materials that cross-link utilizing divalent cations (e.g., $Ca^{+2}$).

Three-dimensional platforms for cells typically rely on inherent physicochemical properties of the polymerization process to generate specific geometries. For example, alginate may be added drop-wise to a solution of cross-linker material, resulting in spherical alginate matrices on which cells are seated. Other approaches for generating three-dimensional cellular cultures with a specific geometry utilize polymerization techniques, such as guided light irradiation during photo polymerization to form specific supporting matrix architectures. In these efforts, polymer properties determine mechanical stability, biocompatibility, transport, and other characteristics that directly affect the ability to maintain cellular growth.

In consequence, the art continues to seek improvements in achieving controlled spatial arrangements of cells, to achieve desirable three-dimensional formations of cellular populations that are created and maintained for their desired purposes, such as investigative efforts, therapeutic interventions, drug development, etc.

SUMMARY

The present disclosure relates to a three-dimensional cell growth containment articles and to methods of making and using such articles.

In one aspect, the disclosure relates to a method of making a three-dimensional cell growth containment article, such method comprising: providing a separable mold body defining a mold cavity therewithin, the separable mold body comprising engageable mold body portions; engaging the engageable mold body portions with one another to constitute the separable mold body, with at least one sacrificial channelizing element compressively retained between the engaged mold body portions so that the sacrificial channelizing element spans the mold cavity; introducing a curable medium into the mold cavity so that the curable medium fills the mold cavity to a predetermined extent, and contacts and circumscribes the sacrificial channelizing element(s) in a bulk volume of the curable medium; at least partially curing the curable medium to form an at least partially cured article; and removing the sacrificial channelizing element(s) from the at least partially cured article so that the at least partially cured article is channelized by the removed sacrificial channelizing element(s), to yield the three-dimensional cell growth containment article containing channel(s) for three-dimensional cell growth therein.

In another aspect, the disclosure relates to a three-dimensional cell growth containment article, comprising a molded body channelized by removal of sacrificial channelizing element(s) therefrom, so that the molded body contains one or more channel(s) therein, with a matrix material in at least one of said channel(s) that is supportive of three-dimensional cell growth in the matrix material.

Other aspects, features and embodiments of the disclosure will be more fully apparent from the ensuing description and appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
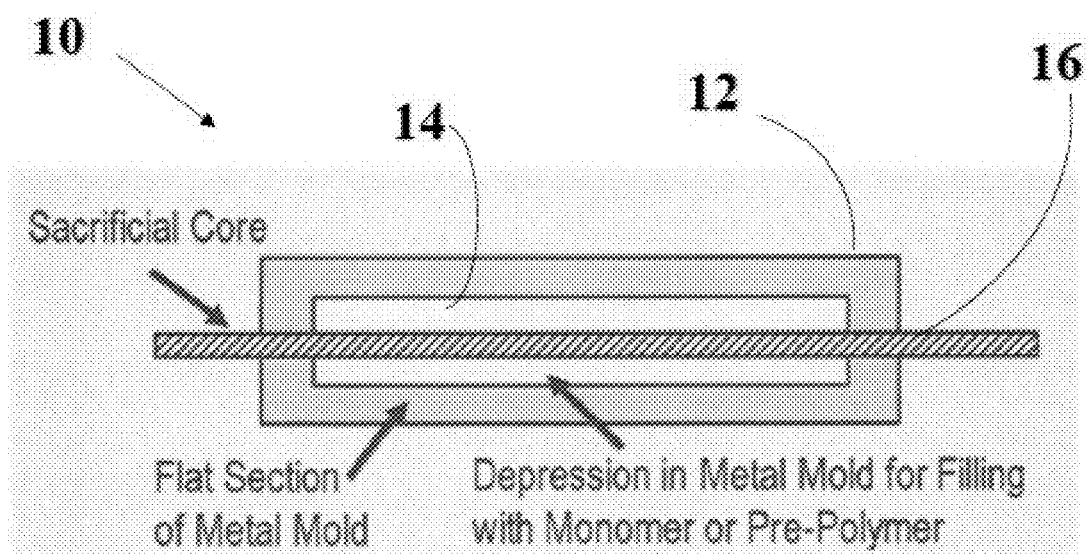
FIG. 1 is a schematic representation of a mold usefully employed for forming a three-dimensional cell growth containment article in accordance with one embodiment of the present disclosure.

The present disclosure relates to three-dimensional cell growth containment articles useful in retentive deployment of cells, e.g., for culturing of cell populations to produce secreted therapeutic agents, and to methods of making and using such articles.

The present inventors have devised a highly efficient manner of precisely depositing cells in a controlled spatial arrangement, and effecting three-dimensional cellular growth, by the provision of retentive structural articles accommodating such deposition and growth, as hereinafter more fully described with respect to such articles and their methods of manufacture and use.

Three-dimensional cell growth containment articles of the present invention enable spatial arrangements of multiple cell types with various polymeric matrices. Such three-dimensional cell growth containment articles are amenable to ready fabrication by use of molding techniques as hereinafter more specifically described, in which molds can be customized with different geometries, injection ports, polymeric materials of construction, and sizes and dimensional characteristics, to support three-dimensional cellular growth in an efficient and effective manner.

Molds utilized for such purpose in accordance with the present disclosure may have multi-compartmental sections to enable injection of different solutions containing different cell types, different monomers, and different pre-polymers. Such molds may be formed with troughs to accommodate and hold injected solutions, with the troughs being of various shapes and/or orientations as desired, e.g., cylindrical troughs. The molds can accommodate sacrificial materials to serve as templates for generating polymeric structures with voids. Alternatively, the mold itself can exist as a sacrificial template, wherein the mold degrades after polymerization of the injected solutions. The mold can accommodate a variety of types of monomers and pre-polymers and mechanisms for polymerization, including ionic cross-linking and covalent cross-linking, such as chain polymerization and step polymerization mechanisms.

In the ensuing description of the three-dimensional cell growth containment article of the present disclosure and the methods of making and using same, it will be recognized that the article may be fabricated and the methods may be performed utilizing any of a variety of features, elements, techniques, and approaches, as described hereafter, and that these various features, elements, techniques, and approaches may be selectively implemented in any suitable implementations and combinations thereof as may be appropriate in a given application of the articles and methods of the present disclosure.

The three-dimensional cell growth containment articles of the present disclosure may be utilized in any applications in which there exists a need to reproducibly generate three-dimensional cellular structures, e.g., islet transplantation for diabetes treatment, transplantation of hormone secreting cells, cellular scaffolds for wound healing, generation of tissue engineering structures to regain structural usefulness for orthopedic applications, etc. The three-dimensional cell growth containment articles of the present disclosure may be constructed of a wide variety of materials in a wide variety of conformations, appropriate to the specific cellular material present in such articles. For example, the three-dimensional cell growth containment article may be provided of a permeable material enabling oxygen and nutrient diffusion into the passage or compartment containing the cells, and the composition and conformation of the article may otherwise be designed for maintaining viability and growth of the cells contained in the article.

The disclosure in one aspect relates to a method of making a three-dimensional cell growth containment article, such method comprising: providing a separable mold body defining a mold cavity therewithin, the separable mold body comprising engageable mold body portions that may be mated with one another to cooperatively form the mold body; engaging the engageable mold body portions with one another to constitute the separable mold body, with at least one sacrificial channelizing element compressively retained between the engaged mold body portions so that the sacrificial channelizing element spans the mold cavity; introducing a curable medium into the mold cavity so that the curable medium fills the mold cavity to a predetermined extent, and contacts and circumscribes the sacrificial channelizing element(s) in a bulk volume of the curable medium; at least partially curing the curable medium to form an at least partially cured article; and removing the sacrificial channelizing element(s) from the at least partially cured article so that the at least partially cured article is channelized by the removed sacrificial channelizing element(s), to yield the three-dimensional cell growth containment article containing channel(s) for three-dimensional cell growth therein. The method described in this paragraph is hereafter referred to as the "broadly described method of the disclosure" and any of the features and aspects hereinafter described for such broadly described method of the disclosure may be selectively aggregated with any other features and aspects described for such broadly described method of the disclosure.

In the broadly described method of the disclosure, the curable medium may be of any suitable type, and may for example comprise an alginate, cellulose, chitosan, collagen, fibrin, glycosaminoglycan, carboxymethylcellulose, a monomer or pre-polymer containing a cell attachment signal agent, acrylate, methacrylate, acrylamide, material that is permeable to cellular nutrients when cells are disposed in the channel(s) of the three-dimensional cell growth containment article, growth factor, hydrogel material, or a combination of two or more of the foregoing. In specific embodiments, the curable medium may comprise polyethylene glycol diacrylate or polyethylene glycol dimethacrylate, e.g., wherein the polyethylene glycol chain has a molecular weight (number average molecular weight) in a range of from 1,000 to 5,000.

A curable medium may be utilized in the broadly described method of the disclosure, wherein the curable medium comprises an alginate having a G:M ratio of guluronic acid (G):mannuronic acid (M) that is greater than 1.5. The at least partially cured curable medium in the broadly described method of the disclosure may for example comprise polylactic-co-glycolic acid (PLGA), polycaprolactone, polyethylene glycol, polylactide, polyglycolide, ethylene-vinyl acetate copolymer, polyvinylalcohol (PVA), or a combination of two or more of the foregoing. In various other embodiments, the at least partially cured curable medium may comprise a natural polymer, such as collagen, fibrin, chitosan, glycosaminoglycan, or combinations of two or more of the foregoing. As another variant of the broadly described method of the disclosure, the at least partially cured curable medium may comprise an immunoprotective polymer.

The curable medium in the broadly described method of the disclosure may comprise a monomer or pre-polymer containing a cell attachment signal agent, e.g., a cell attachment signal agent comprising arginylglycylaspartic acid, or such agent may be added as a part of subsequently introduced fill material to the channel(s) of the article. In other embodiments, the curable medium may comprise a growth factor, such as for example a vascular endothelial growth factor (VEGF) or a fibroblastic growth factor, or such factor or factors may be added as a part of subsequently introduced fill material to the channel(s) of the article. It will be recognized that in the three-dimensional cell growth containment article of the present disclosure and its associated methods of manufacture and use, the curable medium, corresponding cured material, and fill materials may generally comprise any of the specific ingredients variously described herein in connection with specific embodiments of the curable medium, corresponding cured material, or fill material, which are compatible with the article and its methods of manufacture and use. Such ingredients may for example include cell-signaling agents, growth factors, siRNAs, and any other suitable ingredients that control, sustain, mediate, or otherwise affect cells in the three-dimensional cell growth containment article. In a specific implementation, the method of the disclosure may comprise introducing a fill material to the channel(s) of the three-dimensional cell growth containment article, wherein the fill material comprises adherent cells in combination with monomers or pre-polymers that contain a cell attachment signal agent, polymerizing the monomers or pre-polymers to form a cell support matrix whereon the adherent cells attach by action of the cell attachment signal agent, and contacting the cells supported in the cell support matrix with a cell culture medium to produce three-dimensional growth of the cells in the cell support matrix.

In the broadly described method of the disclosure, the three-dimensional cell growth containment article may contain multiple channels. At least some of such multiple channels may be in cell-signaling proximity to one another. The at least partially cured curable medium in the broadly described method of the disclosure may comprise material that is permeable to cellular nutrients when cells are disposed in the channel(s) of the three-dimensional cell growth containment article.

In one embodiment of the broadly described method of the disclosure, the curable medium comprises a hydrogel material. The hydrogel material may be ionically cross-linkable, and may for example comprise an alginate. The alginate may be cross-linkable with divalent cations, such as calcium ($Ca^{+2}$) cations. Accordingly, the broadly described method of the disclosure may be carried out, as comprising introducing into one or more of the channel(s) a mixture of cells and alginate, followed by contacting the three-dimensional cell growth containment article with a cross-linking solution of calcium dichloride or aluminum trichloride to cross-link the alginate in the mixture of cells and alginate, so that the cells are supported in a matrix of cross-linked alginate, and contacting the cells supported in the matrix of cross-linked alginate in the three-dimensional cell growth containment article, with a cell culture medium to produce three-dimensional growth of the cells in the matrix.

The broadly described method of the disclosure may be carried out, wherein the engageable mold body portions are formed of degradable sacrificial material, and the method further comprises degrading the degradable sacrificial material after at least partially curing the curable medium to form the at least partially cured article. In such method, the degrading may comprise at least one of chemically decomposing the degradable sacrificial material, volatilizing the degradable sacrificial material, dissolving the degradable sacrificial material, irradiating the degradable sacrificial material with degradative radiation, and thermally decomposing the degradable sacrificial material. In a specific embodiment, the degradable sacrificial material may be chemically decomposed by hydrolysis thereof.

In various embodiments of the broadly described method of the disclosure, the separable mold body may comprise a port for introducing the curable medium into the mold cavity.

The curable medium and in the broadly described method of the disclosure may be at least partially cured by a curing modality including at least one of ionic cross-linking, covalent cross-linking, hydrolysis, and polymerization.

The sacrificial channelizing element in the broadly described method of the disclosure may comprise a fiber, filament, or cord that is maintained in tension across its spanning extent. The mold cavity may be cylindrical, with the sacrificial channelizing element extending along a centerline of the cylindrical mold cavity.

The broadly described method of the disclosure may be carried out with the additional step of introducing a fill material to the channel(s) of the three-dimensional cell growth containment article. The fill material may comprise at least one of monomer, prepolymer, cells, growth factors, nano materials, small molecule drugs, antibodies, proteins, nucleic acids, nutrients, tracers, bacteria, viruses, and gas-producing substances. In various embodiments, the fill material may comprise a biological material, which may comprise naturally occurring biological material and/or synthetic biological material. The biological material may for example comprise at least one of cells, antibodies, proteins, nucleic acids, bacteria, and viruses. In various embodiments, the fill material comprises cells, e.g., suspension cells, or adherent cells affixed to interior surface of the channel(s) or affixed to materials comprising or comprised in the at least partially cured medium of the three-dimensional cell growth containment article, or affixed to hormone secreting cells.

The cells may be of one or more cell types of corticotropes, gonadotropes, thyrotropes, lactotropes, somatotropes, magnocellular neurosecretory, thyroid epithelial, parafollicular, parathyroid, adrenal gland, macula densa kidney, Leydig, granulosa lutein, theca lutein, peripolar kidney, and mesangial kidney cells. The cells in other embodiments may comprise islets of Langerhans, e.g., one or more cell types of alpha cells, beta cells, delta cells, PP cells, and Epsilon cells. In still other embodiments, the cells may comprise liver cells, e.g., of one or more cell types of hepatocytes, stellate cells, Kupfer cells, and liver endothelial cells. In still other embodiments, the cells may comprise peptide hormone secreting cells, e.g., wherein the peptide hormone secreting cells are one or more cell types of alpha cells, beta cells, corticotropic cells, delta cells, gonadotropin cells, gastric chief cells, lactotropic cells, parafollicular cells, parathyroid cells, somatotropic cells, and thyrotropic cells.

In various embodiments of the broadly described method of the disclosure, the fill material comprises adherent cells in combination with monomers or pre-polymers that contain a cell attachment signal agent, e.g., a cell attachment signal agent comprising arginylglycylaspartic acid. In other embodiments, the curable medium may comprise a growth factor, such as for example a vascular endothelial growth factor (VEGF) or a fibroblastic growth factor.

In various embodiments of the broadly described method of the disclosure, the curable material comprises acrylamide, water, alginate, ammonium persulfate, and tetramethylenediamine (TEMED). Such curable material may be cured at room temperature to polymerize the acrylamide to polyacrylamide to form the at least partially cured article comprising polyacrylamide and non-cross-linked alginate. The method may comprise contacting the at least partially cured article comprising polyacrylamide and non-cross-linked alginate with a curing solution of calcium dichloride or aluminum trichloride to cross-link the alginate, to yield the three-dimensional cell growth containment article as a polymeric structure comprising polyacrylamide and alginate polymer. The method may further comprise sterilizing the three-dimensional cell growth containment article, e.g., by contacting the three-dimensional cell growth containment article with a sterilizing medium, such as alcohol. The method may further comprise conditioning the three-dimensional cell growth containment article in cell media.

The broadly described method of the disclosure may further comprise introducing a fill material to the channel(s) of the three-dimensional cell growth containment article, wherein the fill material comprises adherent cells in combination with monomers or pre-polymers that contain a cell attachment signal agent, polymerizing the monomers or pre-polymers to form a cell support matrix whereon the adherent cells attach by action of the cell attachment signal agent, and contacting the cells supported in the cell support matrix with a cell culture medium to produce three-dimensional growth of the cells in the cell support matrix. In another implementation, the broadly described method of the disclosure may further comprise introducing into one or more of the channel(s) a mixture of cells and alginate, followed by contacting the three-dimensional cell growth containment article with a cross-linking solution of calcium dichloride or aluminum trichloride to cross-link the alginate in the mixture of cells and alginate, so that the cells are supported in a matrix of cross-linked alginate. The method may further comprise contacting the cells supported in the matrix of cross-linked alginate in the three-dimensional cell growth containment article, with a cell culture medium to produce three-dimensional growth of the cells in the matrix.

The present disclosure in another aspect relates to a three-dimensional cell growth containment article, comprising a molded body channelized by removal of sacrificial channelizing element(s) therefrom, so that the molded body contains one or more channel(s) therein, with a matrix material in at least one of said channel(s) that is supportive of three-dimensional cell growth in the matrix material. The article described in this paragraph is hereafter referred to as the "broadly described article of the disclosure" and any of the features and aspects hereinafter described for such broadly described article of the disclosure may be selectively aggregated with any other features and aspects described for such broadly described article of the disclosure.

In the broadly described article of the disclosure, the molded body may comprise a cured material derived from alginate, cellulose, chitosan, carboxymethylcellulose, acrylate, methacrylate, acrylamide, or a combination of two or more of the foregoing. The molded body may for example comprise a cured material derived from polyethylene glycol diacrylate or polyethylene glycol dimethacrylate, e.g., wherein the polyethylene glycol chain has a molecular weight (number average molecular weight) in a range of from 1,000 to 5,000.

In various embodiments of the broadly described article of the disclosure, the molded body may comprise a cured material derived from an alginate having a G:M ratio of guluronic acid (G):mannuronic acid (M) that is greater than 1.5.

In various embodiments of the broadly described article of the disclosure, the molded body may comprise polylactic-co-glycolic acid (PLGA), polycaprolactone, polyethylene glycol, polylactide, polyglycolide, ethylene-vinyl acetate copolymer, or a combination of two or more of the foregoing.

In various embodiments of the broadly described article of the disclosure, the molded body may comprise an immunoprotective polymer.

The broadly described article of the disclosure in various embodiments may have the molded body comprising a cured material derived from a monomer or pre-polymer containing a cell attachment signal agent, e.g., arginylglycylaspartic acid. In other embodiments, the cured material may comprise a growth factor, such as for example a vascular endothelial growth factor (VEGF) or a fibroblastic growth factor.

The broadly described article of the disclosure may contain multiple channels, e.g., in an arrangement in which at least some of the multiple channels are in cell-signaling proximity to one another, and wherein the article comprises a cell attachment signal agent such as arginylglycylaspartic acid.

The molded body of the broadly described article of the disclosure may comprise material that is permeable to cellular nutrients when cells are disposed in the channel(s) of the three-dimensional cell growth containment article.

In various embodiments of the broadly described article of the disclosure, the molded body comprises hydrogel material. The hydrogel material may be ionically cross-linked. The hydrogel material may comprise an alginate.

In various embodiments of the broadly described article of the disclosure, at least one of the channel(s) of the article contains fill material comprising at least one of monomer, prepolymer, cells, growth factors, nano materials, small molecule drugs, antibodies, proteins, nucleic acids, nutrients, tracers, bacteria, viruses, and gas-producing substances. For example, the fill material may comprise a biological material, which may be naturally occurring biological material and/or synthetic biological material. The biological material may comprise at least one of cells, antibodies, proteins, nucleic acids, bacteria, and viruses.

The broadly described article of the disclosure in various embodiments may include fill material comprising cells in the matrix material. The cells may comprise suspension cells and/or the cells may comprise adherent cells affixed to interior surfaces of the channel(s) containing the matrix material. The cells may comprise hormone secreting cells, e.g., wherein the cells are of one or more cell types of corticotropes, gonadotropes, thyrotropes, lactotropes, somatotropes, magnocellular neurosecretory, thyroid epithelial, parafollicular, parathyroid, adrenal gland, macula densa kidney, Leydig, granulosa lutein, theca lutein, peripolar kidney, and mesangial kidney cells. The cells may comprise islets of Langerhans, e.g. of one or more cell types of alpha cells, beta cells, delta cells, PP cells, and Epsilon cells. The cells may comprise liver cells, e.g., one or more cell types of hepatocytes, stellate cells, Kupfer cells, and liver endothelial cells. The cells may comprise peptide hormone secreting cells, e.g., of one or more cell types of alpha cells, beta cells, corticotropic cells, delta cells, gonadotropin cells, gastric chief cells, lactotropic cells, parafollicular cells, parathyroid cells, somatotropic cells, and thyrotropic cells.

The broadly described article of the disclosure may in various embodiments comprise a matrix material, as for example matrix material comprising cross-linked alginate, that further comprises a cell attachment signal agent, e.g., arginylglycylaspartic acid. In other embodiments, the matrix material may comprise a growth factor, such as for example a vascular endothelial growth factor (VEGF) or a fibroblastic growth factor.

The molded body of the broadly described article of the disclosure may in various embodiments comprise polyacrylamide. The molded body may for example comprise polyacrylamide and cross-linked alginate.

The broadly described article of the disclosure in a form amenable to deployment or otherwise in use may be constituted as containing a three-dimensional cell population in the matrix material.

The broadly described article of the disclosure and the broadly described method of the disclosure encompass, in various embodiments, a retrievable three-dimensional cell growth containment article in the form of an insulin production device that is introducible in the body of a subject, e.g., by injection, or other suitable modality of administration. The article in such application may be constructed as a hollow, multi-layered implant that contains a population of islet cells for production of insulin, and is sufficiently permeable for insulin, glucose, and oxygen exchange in the body of the (human or veterinary) subject without allowing antibodies to reach islet cells.

Such insulin production device may include a hollow core in which islet cells suspended in alginate are provided, with RGD for effecting cell adhesion. Such cell-containing core may be circumscribed by an alginate-PA layer for stability, with an outermost layer of high-G alginate, and VEGF-C for vascularization. The outermost layer thereby provides an immunoprotective layer in the structure, and the islet function is supported by the high-G alginate, the presence of RGD, VEGF-C on the surface for vascularization, and $CaO_2$ to generate oxygen.

It will therefore be appreciated that the size, form, and configuration of the channels, passages, and compartments of the three-dimensional cell growth containment article may be selectively varied to provide a desired character and extent of three-dimensional cell growth in the article, as necessary or desirable in a given application of the article.

Referring now to the drawings, FIG. 1 is a top plan view of a half-section of a separable mold body usefully employed for forming a three-dimensional cell growth containment article in accordance with one embodiment of the present disclosure.

As illustrated, the mold 10 includes a half-section mold body 12 shown in top plan view, of generally rectangular configuration, including a correspondingly rectangular cavity 14 therein which in the illustrated plan view surrounds the cavity in the interior volume of the half-section mold body. The half-section mold body illustrated is overlaid with a sacrificial core element 16, being reposed on the flat surface of the half-section mold body, which is engageable with a second half-section mold body (not shown) of corresponding shape to the half-section mold body illustrated, which may be disposed as a lower half-section of the mold. The upper half-section of the mold is symmetrically formed with half-section mold body 12, being inverted with respect to such half-section mold body so that facing flat surfaces of the two half-sections are made in face-to-face contact with one another to enclose the rectangular cavity 14, with the sacrificial core element 16 being compressively retained between the respective half-sections of the mold body.

The respective mold body half-sections may be formed with inlet and outlet ports (not shown in FIG. 1), for introduction of monomer or pre-polymer into the cavity 14 between the respective half-sections of the mold, following which the respective inlet and outlet ports may be closed, and the monomer or pre-polymer composition in the cavity 14 may be subjected to suitable curing conditions, e.g., elevated temperature conditions, anaerobic conditions, or other conditions that may effect reaction and curing of the monomer or pre-polymer into a cured mass.

After the monomer or pre-polymer has been reacted and cured to a corresponding mass defined by the bounding walls of the cavity 14, the separable half-sections of the mold body may be separated from one another to yield a unitary mass of product polymer, having the sacrificial core element 16 extending therethrough. The sacrificial core element 16 may then be removed by any appropriate removal conditions, to provide a corresponding opening in the unitary mass of product polymer. For example, the sacrificial core element 16 may be a material that is amenable to removal from the cured mass of polymer, by grasping of one extended in of the sacrificial core element and intentionally drawing same out of the cured polymer mass to yield the through-bore opening 20 in the resulting polymer article as the three-dimensional cell growth containment article 18.

As another alternative, the sacrificial core elements 16 may be formed of a material that is soluble in a suitable solvent medium which when contacted with the cured mass of polymer leaches away the sacrificial core element to leave the aforementioned through-bore passage in the cured mass of polymer, thereby yielding a three-dimensional cell growth containment article, having a central bore passage within which a cellular population may be introduced for subsequent growth therein.

In the aforementioned method, the half-sections of the mold body may be formed of any suitable material such as for example metal, ceramic, composite material, or other suitable material that is compatible with the monomer or prepolymer composition that is molded in the cavity of the mold body. The sacrificial core element 16 in such method may be aligned in the center of the cavity by applying tension on both ends as the respective half-sections of the mold body are brought into registration alignment with one another. In such manner, the sacrificial core element provides a structure, which when removed, generates a hollow core passage in the product molded body. The hollow core passage then can be filled with cells, as mentioned above, e.g., in combination with a suitable scaffold material, such as another monomer or pre-polymer suitable for such purpose. The cellular population then may be fixed in position by curing of the other monomer or pre-polymer introduced with the cell population into the hollow core passage of the molded article. Alternatively, the monomer or prepolymer may be introduced into the hollow core passage in advance of introducing the cell population thereto, so that a matrix is formed in the hollow core passage, into which the cell population may be introduced.

Figure 2:
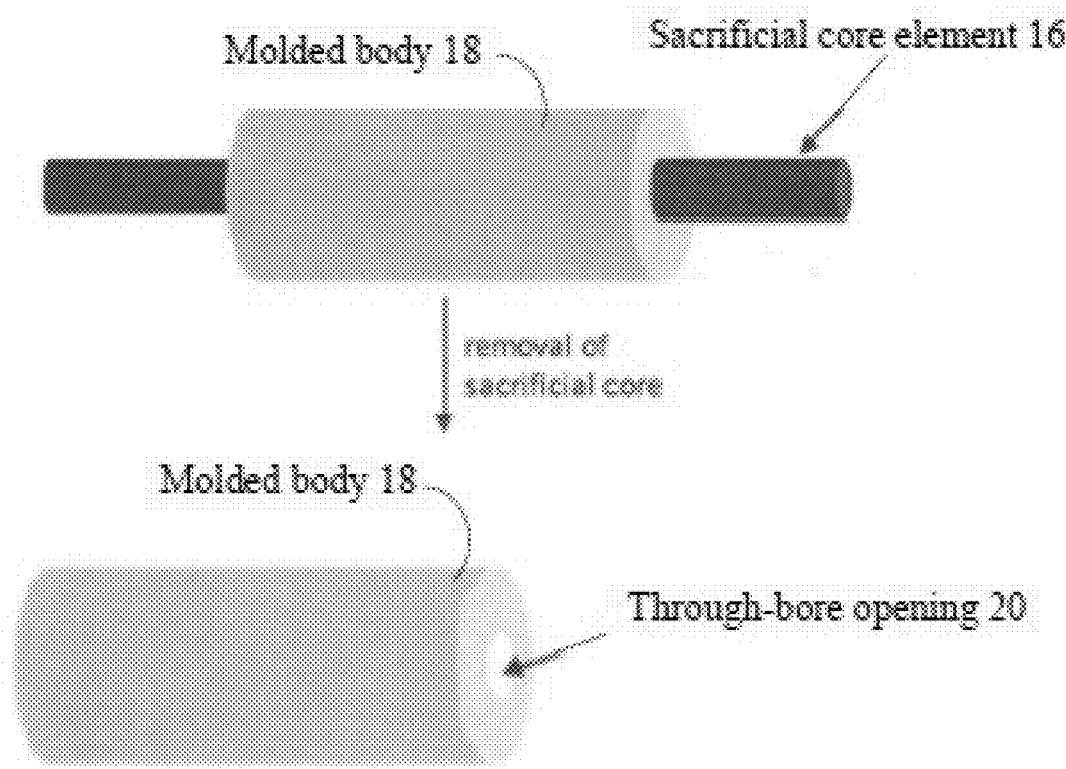
FIG. 2 schematically illustrates the removal of the sacrificial core element from a molded body (polymer structure) to form a through-bore opening as a hollow core passage in the polymer structure of the molded body in the formation of a three-dimensional cell growth containment article according to one embodiment of the present disclosure.

FIG. 2 illustrates the removal of the sacrificial core element 16 from the molded body (polymer structure) to form the through-bore opening 20 as a hollow core passage in the polymer structure of the molded body in the formation of the three-dimensional cell growth containment article 18. The hollow core passage then can be provided with a cellular population introduced into the passage together with any suitable associated material such as scaffolding, cellular nutrients, etc.

The mold that is utilized for forming the three-dimensional cell growth containment article can be designed in any of widely varying ways.

Figure 3:
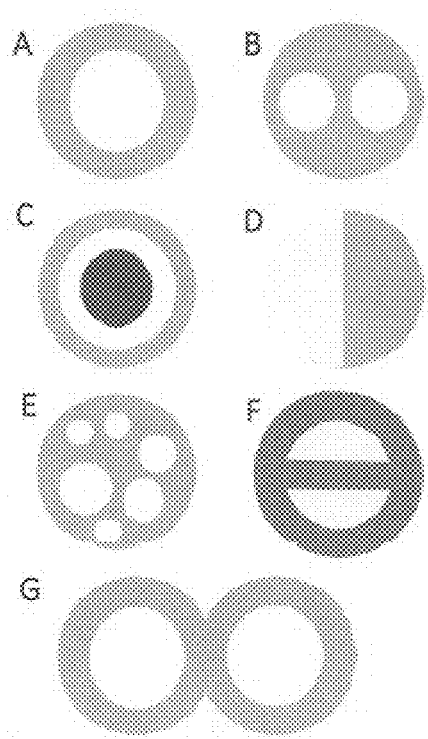
FIG. 3 depicts cross sections of various illustrative polymer structures that may be fabricated with correspondingly configured molds for making three-dimensional cell growth containment articles of the present disclosure.

FIG. 3 depicts cross sections of polymer structures A-G that may be fabricated with correspondingly configured molds. With the exception of cross-section D, of the polymer structures are formed so as to provide interior passages in which the cellular population may be disposed. The cross-section D illustrates a hemi-cylindrical configuration that may be combined with other molded elements to provide one or more interior passages. For example, the hemi-cylindrical molded body of cross-section D may be engaged with a U-shaped channel member secured at its extremities to the flat face of the molded body of cross-section D, to thereby form an enclosed interior volume through the resulting composite structure. In addition, in molded bodies having multiple interior passages, the molded body may be formed of a permeable material allowing infusion of cellular nutrients from one passage containing same to another passage containing the cellular population, in order to maintain viability of the cellular population. In like manner, the molded body may contain an interior passage that is arranged to receive secreted materials, such as secreted therapeutic proteins, as well as waste products such as cellular degradation products, from the cellular population in another interior passage of the molded body.

Thus, the molded body may be provided with multiple compartments, in which each compartment can be at least partially filled with various components, including, without limitation, monomer, pre-polymer, cells, growth factors, nanomaterials, small molecule drugs, antibodies, proteins, nucleic acids, nutrients, tracers, bacteria, viruses, gas-producing substances, and compatible combinations of 2 or more of the foregoing.

In a specific implementation, the three-dimensional cell growth containment article is utilized to support a population of islet cells in one or more passages in the article, for the prevention or treatment of diabetes. For such purpose, the molded body may be employed to form an implant containing islet cells within a reservoir that is encapsulated by a core of polymer in the molded body, with such polymer comprising a biocompatible material capable of maintaining viability of the cells in the molded article.

The three-dimensional cell growth containment article in other applications may be utilized to encapsulate multiple cellular types within a polymeric matrix with controlled spatial arrangement. Cellular types may for example include suspension cells and adherent cells. Specific examples of cells that may be deployed in three-dimensional cell growth containment articles of the present disclosure include, without limitation, hormone secreting cells such as corticotropes, gonadotropes, thyrotropes, lactotropes, somatotropes, magnocellular neurosecretory cells, thyroid epithelial cells, parafollicular cells, parathyroid cells, adrenal gland cells, macula densa cells of the kidney, Leydig cells, granulosa lutein cells, theca lutein cells, peripolar cells of kidney, and mesangial cells of kidney. Langerhans islet cells may be provided in the passages of the three-dimensional cell growth containment articles of the present disclosure, including alpha cells, beta cells, delta cells, PP cells, epsilon cells, and combinations thereof. Additional cell types include liver cells, such as hepatocytes, stellate cells, Kupffer cells, liver endothelial cells, and combinations of two or more of the foregoing. Still further cell types include peptide hormone secreting cells, including alpha cells, beta cells, corticotropic cells, delta cells, gonadotropic cells, gastric chief cells, lactotropic cells, parafollicular cells, parathyroid cells, somatotropic cells, and thyrotropic cells, and combinations of two or more of the foregoing.

Monomers that are used to prepare the polymeric matrix in the three-dimensional cell growth containment articles of the present disclosure may be of any suitable type, and may for example include alginates, cellulose, chitosan, carboxymethylcellulose, acrylate, methacrylates, and acrylamides. Nonlimiting examples of acrylates and methacrylates include polyethylene glycol (PEG) diacrylate and PEG dimethacrylate. In particularly advantageous embodiments, the PEG chain may have a molecular weight in a range of from 1,000 to 5,000 (number average molecular weight). In one preferred embodiment, the alginate has a G:M ratio greater than 1.5. Other nonlimiting examples of polymers suitable for formation of the matrix include poly lactic co-glycolic acid (PLGA), polycaprolactone, PEG, polylactide, polyglycolide, ethylene-vinyl acetate copolymer, and combinations of two or more of the foregoing.

Polymers utilized as support or scaffolding material in the three-dimensional cell growth containment article may be of any suitable type, and may for example be immunoprotective in character to support cellular proliferation and survival. In various implementations, the polymer may be chemically or physically modified to support the specific cells being incorporated in the cell growth containment article. For example, adherent cell lines may be utilized in combination with monomers and or prepolymers that contain a cell attachment signal, such as arginylglycylaspartic acid (RGD). In other implementations, cells may be present together with a growth factor, such as for example a vascular endothelial growth factor (VEGF) or a fibroblastic growth factor. In still other implementations, the cells may be grown in suspension in the three-dimensional cell growth containment article.

In various embodiments, the molded article of the three-dimensional cell growth containment structure may be formed with multiple compartments, in which cells within a scaffolding precursor are injected into a first compartment and a biological agent within a scaffolding precursor is injected into a second compartment. The biological agent may for example include any of growth factors, nanomaterials, small molecule drugs, antibodies, proteins, nucleic acids, nutrients, tracers, bacteria, viruses, gas-producing substances, and combinations of two or more of the foregoing. In such manner, the biological agent may be controllably delivered to the cells or kept in close spatial proximity without contacting the cells. As a specific example, paracrine signaling may be provided by such type of arrangement. As another specific example, multiple compartments in the cell growth containment structure may contain cells of different types that are permitted to grow close to each other, e.g., to enable cell signaling and resultant behaviors to be evaluated.

The features and advantages of the present disclosure are more fully appreciated with reference to the following non-limiting examples.

Example 1

Engineered Mold for Producing a Cylindrical Polymer with a Hollow Core

Figure 4:
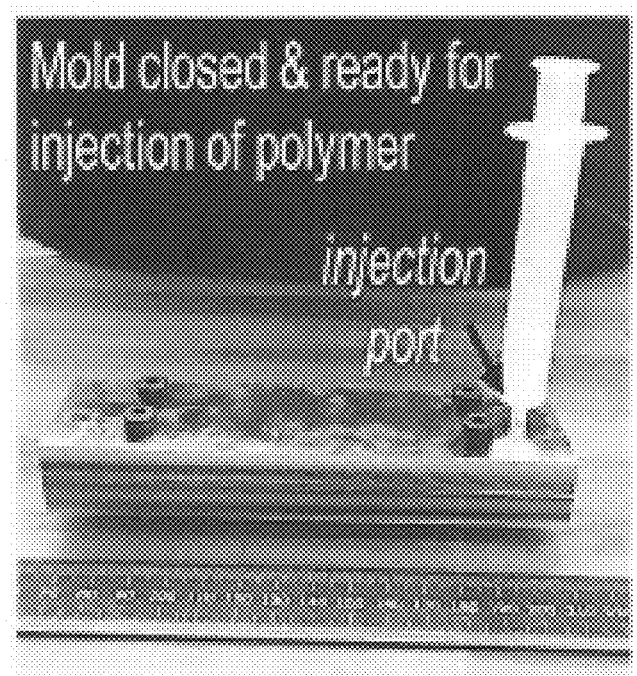
FIG. 4 is a digital camera image of an aluminum mold that was used to prepare a cylindrical cell growth containment article with a hollow core.
Figure 5:
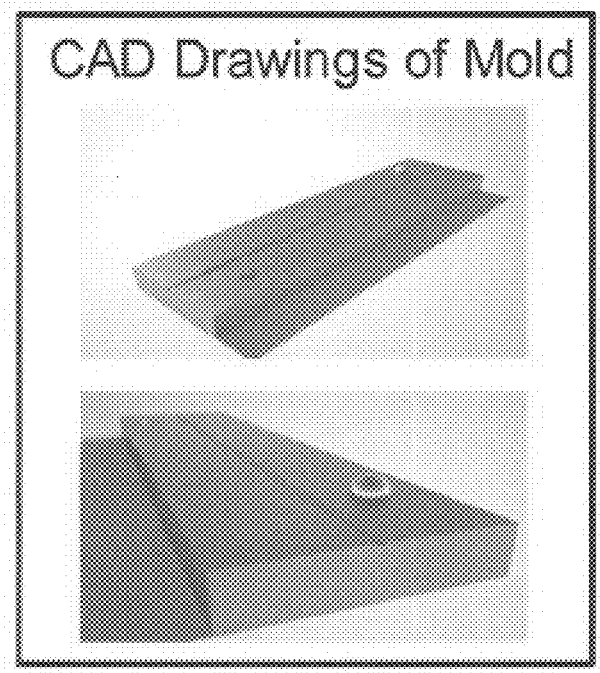
FIG. 5 shows CAD drawings of the mold design of the mold of FIG. 4.
Figure 6:
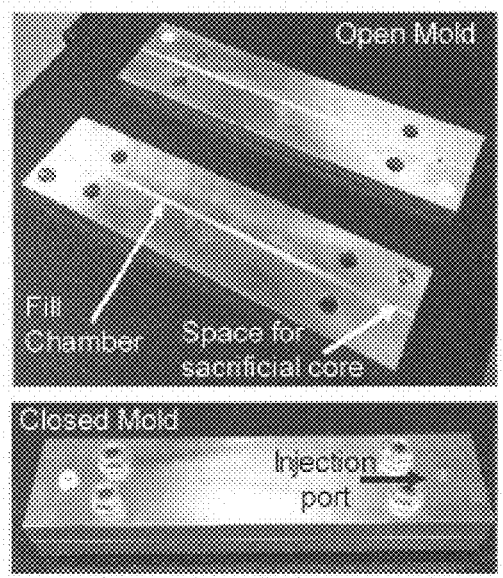
FIG. 6 shows digital camera images of the mold of FIGS. 4 and 5.

FIG. 4 is a digital camera image of an aluminum mold that was used to prepare a cylindrical cell growth containment article with a hollow core. FIG. 5 shows CAD drawings of the mold design and FIG. 6 shows digital camera images of the resulting mold.

A mold was fabricated for filling with selected monomer or prepolymer, as illustrated in FIG. 4. By the use of such mold, a cylindrical polymeric structure with hollow core can be produced, wherein the hollow core provides an interior passage suitable for filling with any of a variety of cellular compositions. The mold was formed of aluminum, with each of the separable half-sections of the mold including an engraved trough arranged to accommodate a sacrificial core element. The sacrificial core element comprised a cord of 1 mm diameter, and the engraved trough measured 2 mm in diameter. The cord was placed between the two aluminum mold half-sections and the mold half-sections were mated with one another, with tensioning of the sacrificial cord prior to tight securement of the half-sections of the mold to one another. By applying adequate tension, the sacrificial cord was centrally aligned within the hollow cylindrical trough formed by the respective engraved troughs of the mated half-sections of the mold.

As shown in FIG. 4, the mold featured an injection port in the upper half-section thereof, which is illustrated with a syringe injector being coupled to such injection port, for introduction of polymer or other curable material into the mold cavity from the syringe injector. FIG. 5 shows the CAD drawings of the mold, in which each mold half-section has a longitudinal cavity formed therein so that when the half-sections of the mold are mated with one another, a corresponding cavity is formed for injection of the polymer or other curable material, to form the molded body of the three-dimensional cell growth containment structure. FIG. 6 shows the open mold half-sections in side-by-side relation to one another, showing the central cavity (fill chamber) and a space at the ends of the half-sections for the sacrificial core element, and the closed mold with the injection port being identified by the arrow in the lower image of the figure.

Example 2

Production of a Structure Comprising a Polymeric Hollow Cylindrical Core

Figure 7:
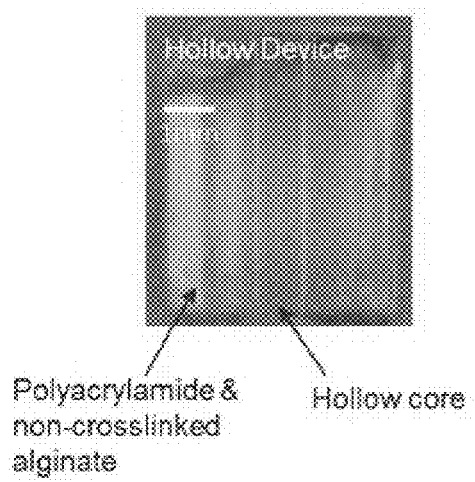
FIG. 7 is a microscopic image of a hollow polymeric cylinder comprising polyacrylamide and non-cross-linked alginate with a hollow core.

A mold of the type described in Example 1 was used to produce a cylindrical structure with a hollow core, using a sacrificial thread element. The aluminum mold was assembled and a monomeric composition was injected into the mold cavity. The monomeric composition comprised 2 mL of acrylamide solution (40% acrylamide in water at an acrylamide:bis-acrylamide ratio of 19:1), 4 mL of 3 wt. % alginate, 100 µL of 10 wt. % ammonium persulfate (APS), and 10 µL of N,N,N',N'-tetramethylethylenediamine (TEMED). After injection of the monomeric composition, the mold was permitted to remain at room temperature for at least 15 minutes, during which time the acrylamide polymerized. After at least 15 minutes, the two portions of the mold were opened and the polymerized cylinder containing the sacrificial core was removed from the mold, and the sacrificial core element was removed, resulting in a hollow polymeric cylinder. FIG. 7 is a microscopic image of the hollow polymeric cylinder comprising polyacrylamide and non-cross-linked alginate with a hollow core.

Next, the hollow cylinder was placed in a cross-linking solution of 50 mM calcium chloride or 50 mM aluminum chloride for 40 minutes to cross-link the alginate in the cylinder.

Figure 8:
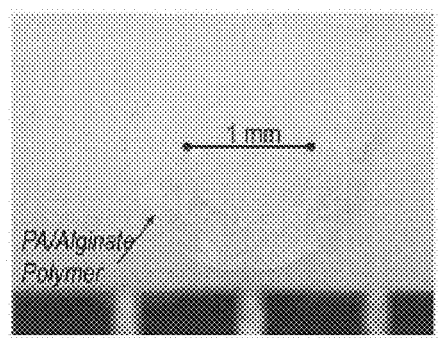
FIG. 8 is a microscopic image of a cross-section of the cylindrical polymer structure comprising polyacrylamide and alginate, and having a hollow core passage with a diameter of 1 mm.

FIG. 8 is a microscopic image of a cross-section of the cylindrical polymer structure comprising polyacrylamide and alginate, and having a hollow core passage with a diameter of 1 mm.

Figure 9:
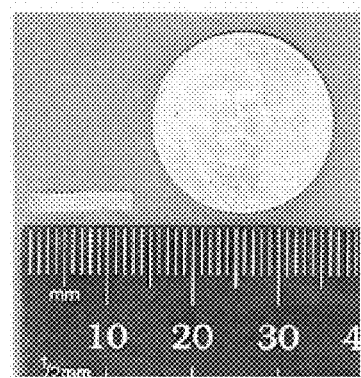
FIG. 9 is a digital camera image of a cylindrical polymer structure of a polyacrylamide/alginate polymer containing a hollow core passage, in which the structure was 12 mm in length with an outer diameter of 2 mm.

FIG. 9 is a digital camera image of the cylindrical polymer structure of the polyacrylamide/alginate polymer containing a hollow core passage, in which the structure was 12 mm in length with an outer diameter of 2 mm.

Figure 10:
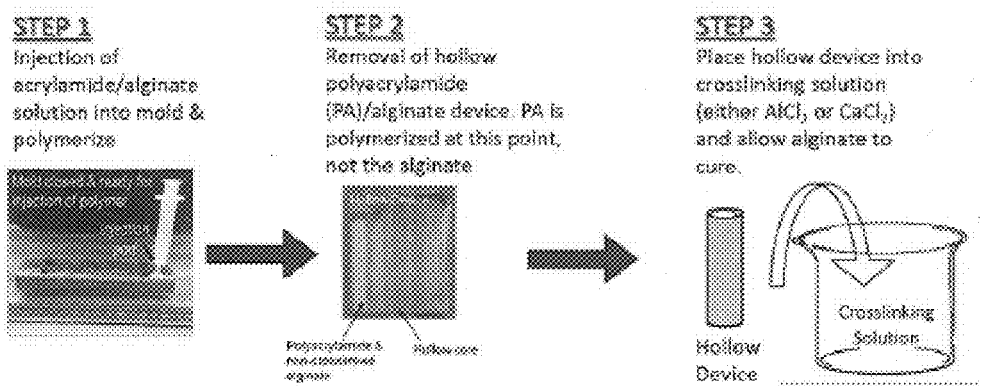
FIG. 10 summarizes the steps involved in forming a hollow core cylindrical polymer structure of a three-dimensional cell growth containment article, according to one embodiment of the disclosure.

FIG. 10 summarizes the steps involved in forming the hollow core cylindrical polymer structure of the three-dimensional cell growth containment article. Step 1 involves injection of the acrylamide/alginate solution into the mold and polymerization thereof. Step 2 involves removal of the hollow polyacrylamide (PA)/alginate molded body, in which PA is polymerized, and the alginate remains unpolymerized. Step 3 involves placement of the hollow core cylindrical polymer structure into a cross-linking solution of either $AlCl_3$ or $CaCl_2$) and allowing the alginate to cure.

Example 3

Production of a Hollow Core Molded Body Article with a Three-Dimensional Cellular Scaffold in the Hollow Core Passage A hollow core cylindrical polymer molded body was formed as described in Example 2, and such molded body, having a 2 mm outer diameter, 1 mm hollow core passage diameter, and length of 12 mm, was placed in 100% ethanol to sterilize the structure. Next, the sterilized molded body was placed in a cellular medium comprising RPMI-1640 supplemented with 10 vol % fetal bovine serum (FBS) for at least 2 hours. During its immersion in ethanol, the molded body shrinks due to expulsion of water therefrom, but it readily rehydrates when placed in the cellular medium. A solution was prepared comprising 9 g of 2% alginate in 150 mM NaCl (1 g of 150 mM NaCl).

Next, a B lymphocyte cell line of Raji cells was suspended in RPMI-1640 cell medium and subsequently mixed with the alginate solution at a ratio of 3:1 of alginate:cells. The final concentration of cells in this mixture was nearly $5 \times 10^5$ cells/mL. The hollow molded article then was injected with approximately 100 µL of such mixture, and the article containing the mixture was incubated in 50 mM $CaCl_2$ in 150 mM NaCl for approximately 15 minutes to effect cross-linking of the core. The resulting cell growth containment article then was transferred to cell culture medium and placed at 37° C. and 5% $CO_2$ to permit cell growth.

Figure 11:
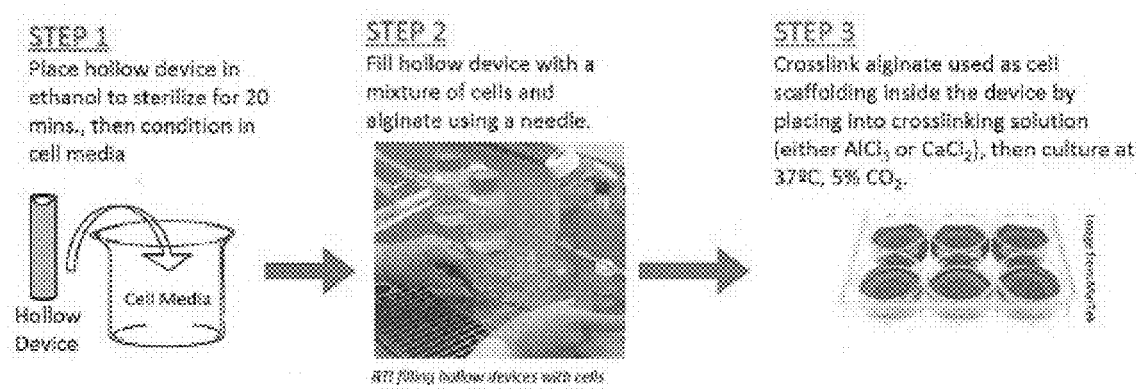
FIG. 11 shows a sequence of 3 steps for producing a three-dimensional cell growth containment article including a core of cells in a three-dimensional scaffold.

FIG. 11 shows the sequence of the foregoing steps for producing a three-dimensional cell growth containment article including a core of cells in a three-dimensional scaffold. Step 1 involves placement of the hollow molded device in ethanol for 20 minutes to effect sterilization, followed by conditioning in cell medium. Step 2 involves filling the molded hollow body with a mixture of cells and alginate using a needle, and Step 3 involves cross-linking the alginate used as cellular scaffolding in the molded article hollow passage, by placing the molded article into cross-linking solution (either aluminum chloride or calcium chloride solution), followed by culturing at 37° C. and 5% $CO_2$ ambient.

Figure 12:
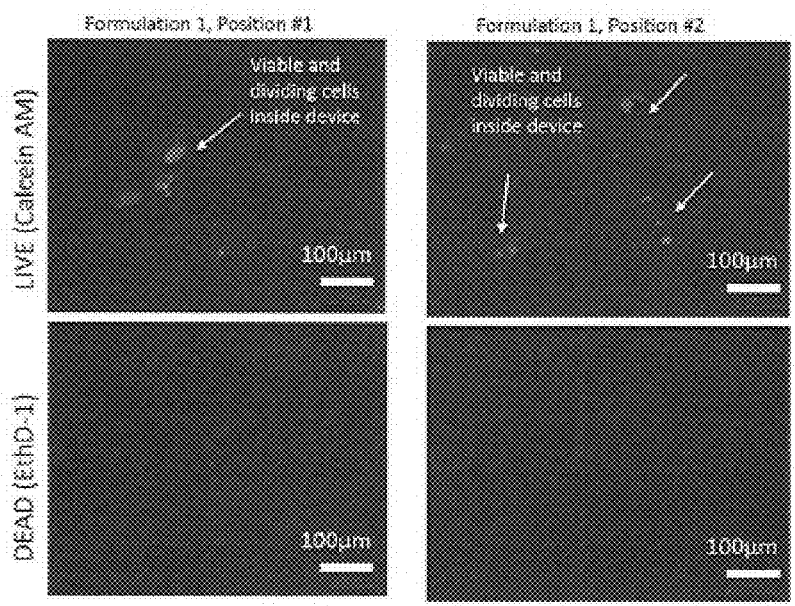
FIG. 12 shows the results after culturing Raji cells in a three-dimensional cell growth containment article for 3 days, in fluorescence images of Raji cells in the interior of the article, as stained with a Live-Dead staining kit.

FIG. 12 shows the results after culturing the Raji cells in the three-dimensional cell growth containment article for 3 days, in fluorescence images of Raji cells in the interior of the article, as stained with a Live-Dead staining kit. The images show fluorescence from calcein AM (green fluorescence), which indicated that the cells were alive. Conversely, no fluorescence resulted from ethidium (which produces red fluorescence), which indicated minimal dead cells in the cell growth containment article.

Figure 13:
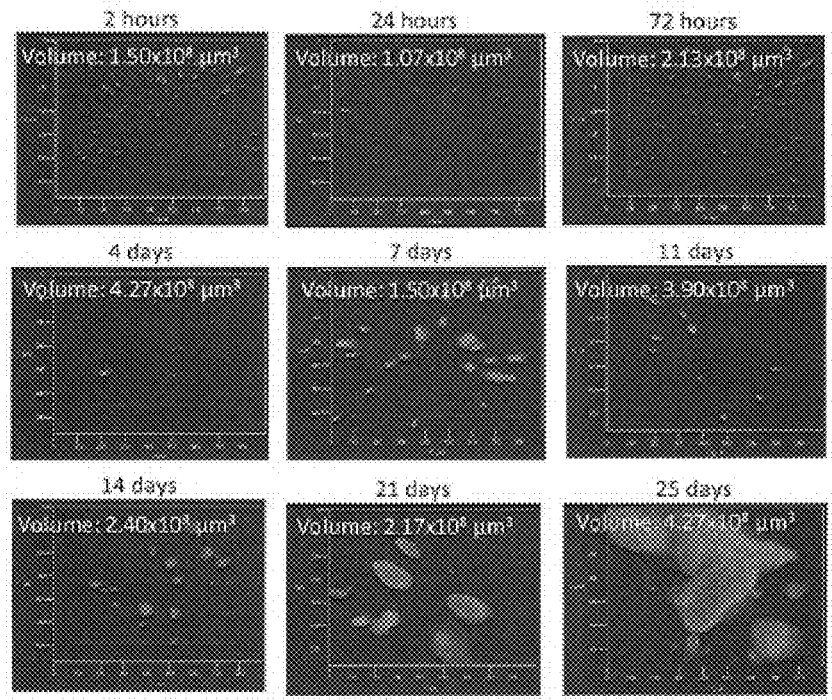
FIG. 13 shows RIN-5F cells alive and proliferating in a three-dimensional cell growth containment article after 25 days.

FIG. 13 shows beta cell line RIN-5F cells alive and proliferating in the three-dimensional cell growth containment article after 25 days. The cell growth containment article contained alginate cross-linked with calcium chloride, as the support matrix for the cells. Fluorescence images are shown of the RIN-5F cells stained with Live-Dead staining kit, in the interior of the cell growth containment article. The images show fluorescence from calcein AM (green), which indicates the cells are alive. Conversely, no fluorescence was observed resulting from ethidium (red), thereby indicating minimal dead cells.

Figure 14:
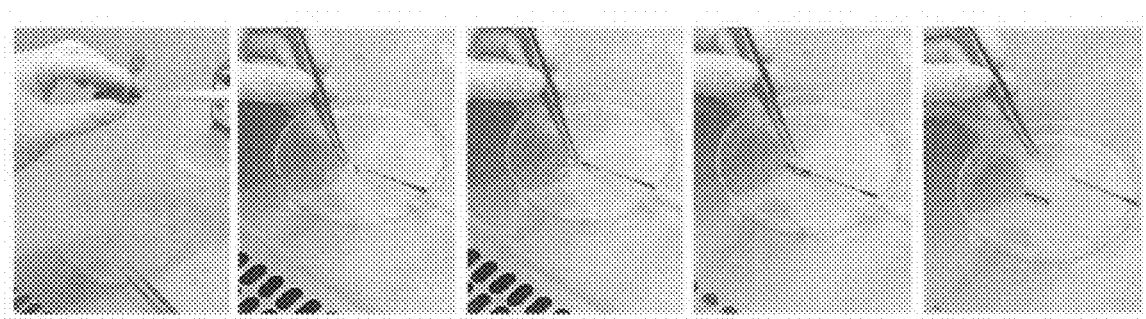
FIG. 14 shows steps for loading a cell mixture into a three-dimensional cell growth containment article, using a solution representing a surrogate for cells for purposes of illustration.

FIG. 14 shows the steps for loading a cell mixture into the three-dimensional cell growth containment article, using a solution representing a surrogate for cells for purposes of illustration. Step 1 illustrates a pipette tip being loaded with 1:3 trypan blue and 2.22% alginate (pre-warmed). In Step 2, the pipette tip is inserted into the three-dimensional cell growth containment article passage. In Step 3, the three-dimensional cell growth containment article is carefully loaded with the alginate-trypan blue solution. In Step 4, the three-dimensional cell growth containment article has been loaded with the hollow core passage being filled. In Step 5, the three-dimensional cell growth containment article in loaded condition is ready for deployment.

While the disclosure has been set forth herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the disclosure as hereinafter claimed is intended to be broadly construed and interpreted, as including all such variations, modifications and alternative embodiments, within its spirit and scope.

What is claimed is:

1. A method of making a three-dimensional cell growth containment article, said method comprising:
    engaging mold body portions with one another to constitute a separable mold body defining a mold cavity therewithin between the engaged mold body portions with at least one sacrificial channelizing element compressively retained between the engaged mold body portions so that the sacrificial channelizing element spans the mold cavity;
    introducing a curable medium into the mold cavity so that the curable medium fills the mold cavity to a predetermined extent, and contacts and circumscribes the sacrificial channelizing element(s) in a bulk volume of the curable medium, the curable medium comprising a polymerizable monomer or prepolymer, and a cross-linkable material;
    polymerizing the polymerizable monomer or prepolymer of the curable medium to form a polymerized article comprising the cross-linkable material and containing the at least one sacrificial channelizing element;
    removing the polymerized article from the mold cavity and removing the sacrificial channelizing element(s) from the polymerized article so that the polymerized article is channelized by the removed sacrificial channelizing element(s);
    cross-linking the cross-linkable material in the channelized polymerized article;
    introducing a fill material to one or more channel(s) in the channelized polymerized article after said cross-linking, the fill material comprising cells and a curable cell support matrix material;
    curing the curable cell support matrix material in the channel(s) to form a cured matrix supporting the cells in the channel(s); and
    contacting the cells supported in the cured matrix in the channel(s) with a cell culture medium, to yield the three-dimensional cell growth containment article containing channel(s) for three-dimensional cell growth therein.

2. The method of claim 1, wherein the curable medium comprises: an alginate; cellulose; chitosan; collagen; fibrin; glycosaminoglycan; carboxymethylcellulose; a monomer or pre-polymer containing a cell attachment signal agent; acrylate; methacrylate; acrylamide; material that is permeable to cellular nutrients; growth factor; hydrogel material; or a combination of two or more of the foregoing.

3. The method of claim 1, wherein the curable medium when cured comprises: polylactic-co-glycolic acid (PLGA); polycaprolactone; polyethylene glycol; polylactide; polyglycolide; ethylene-vinyl acetate copolymer; an immunoprotective polymer, or a combination of two or more of the foregoing.

4. The method of claim 1, wherein the three-dimensional cell growth containment article contains multiple channels, and wherein the curable medium comprises arginylglycylaspartic acid.

5. The method of claim 1, wherein the curable medium when cured comprises an alginate cross-linked with calcium ($Ca^{+2}$) cations.

6. The method of claim 1, wherein the mold body portions are formed of degradable sacrificial material, and the method further comprises degrading the degradable sacrificial material after polymerizing the polymerizable monomer or prepolymer of the curable medium, wherein the degrading comprises at least one of chemically decomposing the degradable sacrificial material, volatilizing the degradable sacrificial material, dissolving the degradable sacrificial material, irradiating the degradable sacrificial material with degradative radiation, and thermally decomposing the degradable sacrificial material.

7. The method of claim 1, wherein the sacrificial channelizing element comprises a fiber, filament, or cord that is maintained in tension across its spanning extent.

8. The method of claim 1, wherein said fill material comprises at least one of monomer, prepolymer, cells, growth factors, nano materials, drugs, antibodies, proteins, nucleic acids, nutrients, tracers, bacteria, viruses, and gas-producing substances.

9. The method of claim 1, wherein said cells are of one or more cell types of corticotropes, gonadotropes, thyrotropes, lactotropes, somatotropes, magnocellular neurosecretory, thyroid epithelial, parafollicular, parathyroid, adrenal gland, macula densa kidney, Leydig, granulosa lutein, theca lutein, peripolar kidney, and mesangial kidney cells.

10. The method of claim 1, wherein the curable material comprises acrylamide, water, alginate, ammonium persulfate, and tetramethylenediamine (TEMED).

11. The method of claim 1, wherein said fill material comprises adherent cells in combination with monomers or pre-polymers that contain a cell attachment signal agent.

12. The method of claim 1, wherein the curable cell support matrix material comprises alginate, and curing thereof comprises contacting with a cross-linking solution of calcium dichloride or aluminum trichloride to cross-link the alginate, so that the cells are supported in a cured matrix of cross-linked alginate.

\* \* \* \* \*